United States Patent [19]
Peglion et al.

[11] Patent Number: 6,153,640
[45] Date of Patent: Nov. 28, 2000

[54] BENZO[3,4]CYCLOBUTA[1,2-C]PYRROLE COMPOUNDS

[75] Inventors: Jean-Louis Peglion, Le Vesinet; Bertrand Goument, Viroflay; Aimée Dessinges, Rueil Malmaison; Mark Millan, Le Pecq; Jean-Michel Rivet, Nanterre; Anne Dekeyne, Saint Remy les Chevreuses, all of France

[73] Assignee: Adir et Compagnie, Courbevoie, France

[21] Appl. No.: 09/533,684

[22] Filed: Mar. 23, 2000

[30] Foreign Application Priority Data

Mar. 26, 1999 [FR] France .................................. 99 03811

[51] Int. Cl.[7] ...................... A61K 31/403; C07D 209/58; C07D 209/70
[52] U.S. Cl. ............................................. 514/411; 548/427
[58] Field of Search ............................... 548/427; 514/411

[56] References Cited

U.S. PATENT DOCUMENTS 4,622,405  11/1986  DeBernardis et al. .................. 548/427

*Primary Examiner*—Laura L. Stockton
*Attorney, Agent, or Firm*—The Firm of Hueschen and Sage

[57] ABSTRACT

A compound of formula (I):

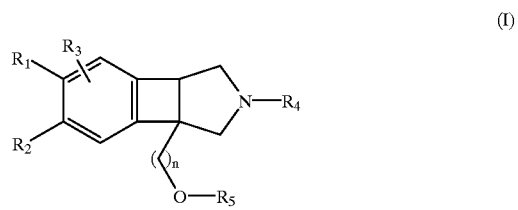

wherein:

$R_1$, $R_2$ and $R_3$, which may be the same or different, represent a group as defined in the description, $R_4$ represents hydrogen, alky, alkenyl, alkynyl, cycloalkyl, cycloalkylalkyl, aryl, arylalkyl, heterocycloalkyl, heterocycloalkylalkyl, heteroaryl, or heteroarylalkyl, $R_5$ represents aryl, or heteroaryl, each optionally substituted, n is an integer from 1 to 3 inclusive, their isomers and addition salts thereof with a pharmaceutically-acceptable acid or base, and medicinal products containing the same are usefull in the treatment of disease like depression, panic attacks, obsessive-compulsive disorders, phobias, impulsive disorders, drug abuse or anxiety.

14 Claims, No Drawings

BENZO[3,4]CYCLOBUTA[1,2-C]PYRROLE COMPOUNDS

FIELD OF THE INVENTION

The present invention relates to new benzo[3,4]cyclobuta[1,2-c]pyrrole compounds. The compounds of the present invention act as powerful inhibitors of serotonin reuptake.

As such, they may be used therapeutically in the treatment of depression, panic attacks, obsessive-compulsive disorders, phobias, impulsive disorders, drug abuse and anxiety.

The results of microdialysis experiments carried out on the frontal cortex show the value of the products of the present invention in treating different pathologies of the central nervous system. Because they bring about, in that area, an increase in the release of serotonin, they are entirely suited to use in pathologies which are associated with a defect in the transmission of that neurotransmitter.

Furthermore, tests carried out on aggressive mice allow the anti-impulsive and anxiolytic properties of the products of the invention to be demonstrated.

DETAILED DESCRIPTION OF THE INVENTION

More specifically, the present invention relates to compounds of formula (I), having a cis ring junction:

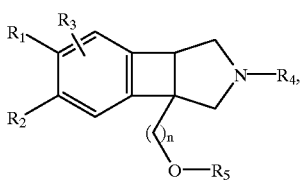

(I)

wherein:

R$_1$, R$_2$ and R$_3$, which may be the same or different, each independently of the others represents a group selected from a hydrogen atom, a halogen atom, a linear or branched (C$_1$–C$_6$)alkyl group, a linear or branched (C$_2$–C$_6$)alkenyl group, a linear or branched (C$_2$–C$_6$)alkynyl group, a hydroxy group, a linear or branched (C$_1$–C$_6$)alkoxy group, a cycloalkyl group, a cycloalkyl-(C$_1$–C$_6$)alkyl group in which the alkyl moiety is linear or branched, an aryl group, an aryl-(C$_1$–C$_6$)alkyl group in which the alkyl moiety is linear or branched, an aryloxy group, an aryl-(C$_1$–C$_6$)alkoxy group in which the alkoxy moiety is linear or branched, a linear or branched (C$_1$–C$_6$)trihaloalkyl group, a linear or branched (C$_1$–C$_6$)trihaloalkoxy group, a cyano group, a nitro group, and a group of formula —OSO$_2$CH$_3$, —OSO$_2$CF$_3$, —NR$_6$R$_7$ or —CO$_2$R$_6$ wherein R$_6$ and R$_7$, which may be the same or different, each independently of the other represents a hydrogen atom, a linear or branched (C$_1$–C$_6$)alkyl group, a linear or branched (C$_2$–C$_6$)alkenyl group, a linear or branched (C$_2$–C$_6$) alkynyl group, a cycloalkyl group, a cycloalkyl-(C$_1$–C$_6$)alkyl group in which the alkyl moiety is linear or branched, an aryl group or an aryl-(C$_1$–C$_6$)alkyl group in which the alkyl moiety is linear or branched, or two of R$_1$, R$_2$ and R$_3$ in adjacent positions represent, together with the common atoms of the benzene ring to which they are bonded, a saturated or unsaturated (C$_4$–C$_8$)-ring system wherein one or two carbon atoms is/are optionally replaced by one or two hetero atoms, which may be the same or different, selected from oxygen, nitrogen and sulphur, it being understood that in the case where two of R$_1$, R$_2$ and R$_3$ in adjacent positions have the meaning mentioned hereinbefore, the remaining group R$_1$ or R$_2$ or R$_3$ takes one of the above-mentioned individual definitions of those groups, R$_4$ represents a group selected from a hydrogen atom, a linear or branched (C$_1$–C$_6$)alkyl group, a linear or branched (C$_2$–C$_6$)alkenyl group, a linear or branched (C$_2$–C$_6$)alkynyl group, a cycloalkyl group, a cycloalkyl-(C$_1$–C$_6$)alkyl group in which the alkyl moiety is linear or branched, an aryl group, an aryl-(C$_1$–C$_6$) alkyl group in which the alkyl moiety is linear or branched, a heterocycloalkyl group, a heterocycloalkyl-(C$_1$–C$_6$)alkyl group in which the alkyl moiety is linear or branched, a heteroaryl group and a heteroaryl-(C$_1$–C$_6$)alkyl group in which the alkyl moiety is linear or branched, R$_5$ represents an aryl group, an optionally substituted aryl group, a heteroaryl group or an optionally substituted heteroaryl group, n represents an integer from 1 to 3 inclusive, their isomers and addition salts thereof with a pharmaceutically acceptable acid or base, a cycloalkyl group being understood to mean a (C$_3$–C$_8$)-ring system, which may be mono- or bi-cyclic, optionally having one or more unsaturated bond(s), the said unsaturated bond(s) not conferring an aromatic character on the ring system, which is optionally substituted by one or more groups, which may be the same or different, selected from a halogen atom and a linear or branched (C$_1$–C$_6$)alkyl group, a heterocycloalkyl group being understood to mean an optionally substituted cycloalkyl group as defined hereinbefore and containing, in the ring system, one, two or three hetero atoms, which may be the same or different, selected from oxygen, nitrogen and sulphur, furthermore, an aryl group being understood to mean a phenyl, naphthyl, dihydronaphthyl, tetrahydronaphthyl, indenyl or indanyl group, and an optionally substituted aryl group being understood to mean an aryl group, as defined, optionally substituted by one or more groups, which may be the same or different, selected from halogen, hydroxy, linear or branched (C$_1$–C$_6$)alkyl, linear or branched (C$_1$–C$_6$) alkoxy, linear or branched (C$_1$–C$_6$)alkenyl, cycloalkyl, adamantyl, cycloalkyl-(C$_1$–C$_6$)alkyl in which the alkyl moiety is linear or branched, aryl, aryl-(C$_1$–C$_6$)alkyl in which the alkyl moiety is linear or branched, aryloxy, aryl-(C$_1$–C$_6$)alkoxy in which the alkoxy moiety is linear or branched, linear or branched (C$_1$–C$_6$) trihaloalkyl, linear or branched (C$_1$–C$_6$)trihaloalkoxy, cyano, nitro, oxo, and groups of formulae —OSO$_2$CH$_3$, —OSO$_2$CF$_3$, —NR$_6$R$_7$ and —CO$_2$R$_6$ wherein R$_6$ and R$_7$ are as defined for formula (I), a heteroaryl group being likewise understood to mean an aryl group as defined hereinbefore containing one, two or three hetero atoms, which may be the same or different, selected from oxygen, nitrogen and sulphur, and an optionally substituted heteroaryl group being understood to mean a heteroaryl group as defined hereinbefore optionally substituted by one or more groups, which may be the same or different, as defined for substitution of the aryl groups.

Among the pharmaceutically acceptable acids there may be mentioned, without implying any limitation, hydrochloric acid, hydrobromic acid, sulphuric acid, phosphonic acid, acetic acid, trifluoroacetic acid, lactic acid, pyruvic acid, malonic acid, glutaric acid, succinic acid, fumaric acid, tartaric acid, maleic acid, citric acid, ascorbic acid, oxalic acid, methanesulphonic acid, camphoric acid etc.

Among the pharmaceutically acceptable bases there may be mentioned, without implying any limitation, sodium hydroxide, potassium hydroxide, triethylamine, tert-butylamine etc.

Preferred substituents $R_5$ according to the invention are heteroaryl groups. According to an advantageous embodiment, preferred groups $R_5$ are the groups methylenedioxyphenyl and ethylenedioxyphenyl.

According to advantageous embodiment of the invention, n preferably represents an integer equal to 1. According to another advantageous embodiment of the invention, n preferably represents an integer equal to 2.

Preferred substituents $R_4$ according to the invention are a hydrogen atom, linear or branched ($C_1$–$C_6$)alkyl groups and aryl-($C_1$–$C_6$)alkyl groups in which the alkyl moiety is linear or branched.

Preferred compounds of the invention are:
cis-3a-[(3,4-methylenedioxyphenoxy)-methyl]-2,3,3a,7b-tetrahydro-1H-benzo[3,4]-cyclobuta[1,2-c]pyrrole,
cis-2-benzyl-5-methoxy-3a-[(3,4-methylenedioxyphenoxy)-methyl]-2,3,3a,7b-tetrahydro-1H-benzo[3,4]cyclobuta[1,2-c]pyrrole,
cis-5-methoxy-3a-[(3,4-methylenedioxyphenoxy)-methyl]-2,3,3a,7b-tetrahydro-1H-benzo[3,4]cyclobuta[1,2-c]pyrrole,
cis-5-methoxy-2-methyl-3a-[(3,4-methylenedioxyphenoxy)-methyl]-2,3,3a,7b-tetrahydro-1H-benzo[3,4]cyclobuta[1,2-c]pyrrole,
cis-6-trifluoromethyl-3a-[(3,4-methylenedioxyphenoxy)-methyl]-2,3,3a,7b-tetrahydro-1H-benzo[3,4]cyclobuta[1,2-c]pyrrole,
and cis-6-fluoro-3a-[(3,4-methylenedioxyphenoxy)-methyl]-2,3,3a,7b-tetrahydro-1H-benzo[3,4]cyclobuta[1,2-c]pyrrole.

The isomers and addition salts with a pharmaceutically acceptable acid or base of the preferred compounds form an integral part of the invention.

The invention relates also to a process for the preparation of compounds of formula (I), which process is characterised in that there is used as starting material a compound of formula (II):

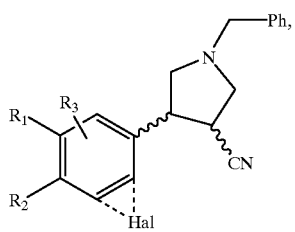
(II)

wherein $R_1$, $R_2$ and $R_3$ are as defined for formula (I) and Hal represents a halogen atom, the said halogen atom being attached to either of the carbon atoms of the benzene ring, which compounds of formula (II) are subjected to the action of sodium amide in liquid ammonia to yield the compounds of formula (III), having a cis ring junction,

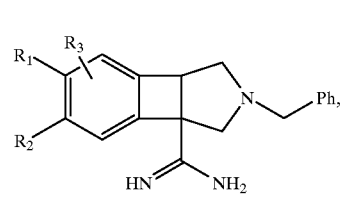
(III)

wherein $R_1$, $R_2$ and $R_3$ are as defined for formula (I), which compounds of formula (III) are treated with a mineral base, in an aqueous alcoholic medium, to yield the compounds of formula (IV), having a cis ring junction,

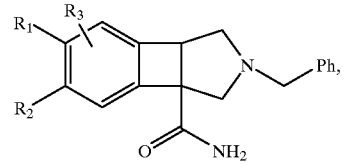
(IV)

wherein $R_1$, $R_2$ and $R_3$ are as defined for formula (I), which compounds of formula (IV) are converted, by means of an acetal of N,N-dimethylformamide of formula (V)

$(CH_3)_2N\ CH(OG)_2$ (V), wherein G represents a linear or branched ($C_1$–$C_6$)alkyl, a benzyl or a cyclohexyl group, into an ester of formula (VI), having a cis ring junction,

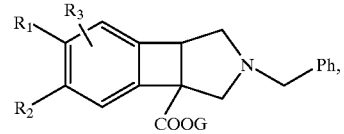
(VI)

wherein $R_1$, $R_2$, $R_3$ and G are as defined hereinbefore, which compounds of formula (VI) are reduced, under conventional conditions of organic synthesis, to an alcohol of formula (VII), having a cis ring junction,

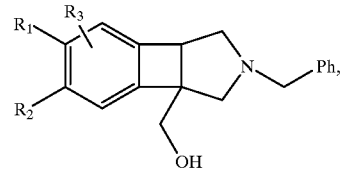
(VII)

wherein $R_1$, $R_2$ and $R_3$ are as defined hereinbefore, which compounds of formula (VII) are:
either treated, according to the conditions of the Mitsunobu reaction, with a compound of formula (VIII)

$R_5$–OH (VIII), wherein $R_5$ is as defined for formula (I), to yield the compounds of formula (I/a) having a cis ring junction, a particular case of the compounds of formula (I):

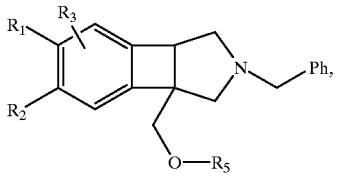
(I/a)

wherein $R_1$, $R_2$, $R_3$ and $R_5$ are as defined hereinbefore, which compounds of formula (I/a) may be debenzylated by one of the methods conventionally used in organic synthesis, to yield the compounds of formula (I/b), having a cis ring junction, a particular case of the compounds of formula (I):

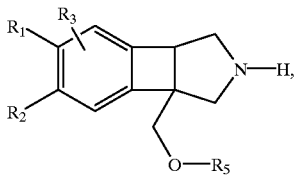
(I/b)

wherein $R_1$, $R_2$, $R_3$ and $R_5$ are as defined hereinbefore, which compounds of formula (I/b) may be:

either converted, by treating with formaldehyde in the presence of sodium cyanoborohydride, into compounds of formula (I/c), having a cis ring junction, a particular case of the compounds of formula (I):

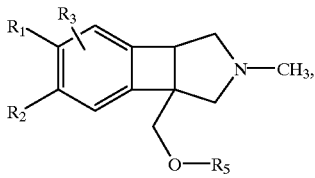
(I/c)

wherein $R_1$, $R_2$, $R_3$ and $R_5$ are as defined hereinbefore, or treated, under conventional conditions of organic synthesis, with a compound of formula (IX):

$$R'_4-Z \quad \text{(IX)},$$

wherein $R'_4$ has the same meanings as $R_4$ except hydrogen and benzyl, and Z represents a leaving group customarily used in organic synthesis, to yield the compounds of formula (I/d), having a cis ring junction, a particular case of the compounds of formula (I):

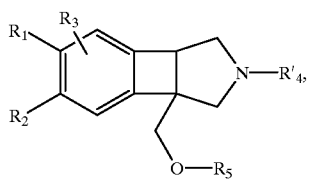
(I/d)

wherein $R_1$, $R_2$, $R_3$, $R'_4$ and $R_5$ are as defined hereinbefore, or converted, by a succession of conventional reactions, into compounds of formula (X), having a cis ring junction,

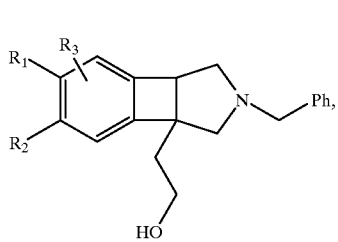
(X)

wherein $R_1$, $R_2$ and $R_3$ are as defined hereinbefore, which compounds of formula (X) are treated, according to the conditions of the Mitsunobu reaction, with a compound of formula (VIII):

$$R_5\text{-OH} \quad \text{(VIII)},$$

wherein $R_5$ is as defined hereinbefore,
to yield the compounds of formula (I/e), having a cis ring junction, a particular case of the compounds of formula (I):

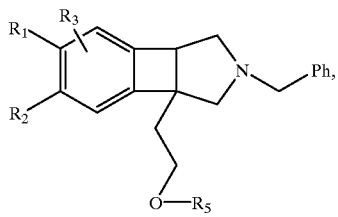
(I/e)

wherein $R_1$, $R_2$, $R_3$ and $R_5$ are as defined hereinbefore, which compounds of formula (I/e) may be debenzylated by one of the methods conventionally used in organic synthesis, to yield the compounds of formula (I/f), having a cis ring junction, a particular case of the compounds of formula (I):

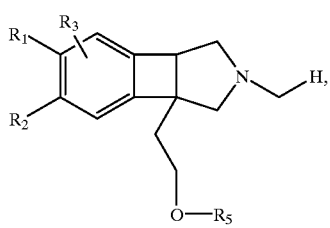
(I/f)

wherein $R_1$, $R_2$, $R_3$ and $R_5$ are as defined hereinbefore, which compounds of formula (I/f) may be:
either converted, by treating with formaldehyde in the presence of sodium cyanoborohydride, into compounds of formula (I/g), having a cis ring junction, a particular case of the compounds of formula (I):

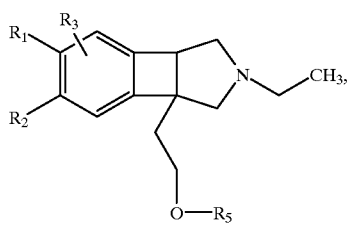

(I/g)

wherein $R_1$, $R_2$, $R_3$ and $R_5$ are as defined hereinbefore,
or treated, under conventional conditions of organic synthesis, with a compound of formula (IX):

R'$_4$-Z          (IX), wherein R'$_4$ has the same meanings as $R_4$ except hydrogen and benzyl, and Z represents a leaving group customarily used in organic synthesis,
to yield the compounds of formula (I/h), having a cis ring junction, a particular case of the compounds of formula (I):

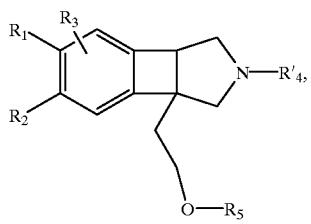

(I/h)

wherein $R_1$, $R_2$, $R_3$, R'$_4$ and $R_5$ are as defined hereinbefore,
or converted, by a succession of conventional reactions, into compounds of formula (XI), having a cis ring junction:

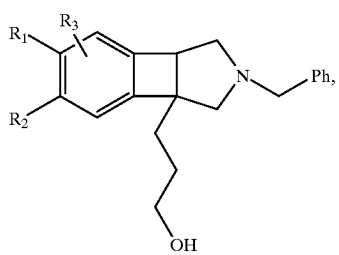

(XI)

wherein $R_1$, $R_2$ and $R_3$ are as defined hereinbefore,
which compounds of formula (XI) can be, as well, obtained by a succession of conventional reactions from compounds of formula (X),
which compounds of formula (XI) are treated, according to the conditions of the Mitsunobu reaction, with a compound of formula (VIII):

R$_5$-OH          (VIII), wherein $R_5$ is as defined hereinbefore,
to yield the compounds of formula (I/i), having a cis ring junction, a particular case of the compounds of formula (I):

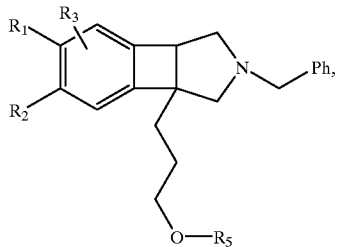

(I/i)

wherein $R_1$, $R_2$, $R_3$ and $R_5$ are as defined hereinbefore,
which compounds of formula (I/i) may be debenzylated by one of the methods conventionally used in organic synthesis to yield the compounds of formula (I/j), having a cis ring junction, a particular case of the compounds of formula (I):

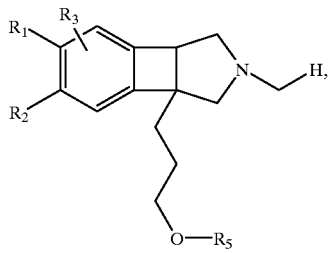

(I/j)

wherein $R_1$, $R_2$, $R_3$ and $R_5$ are as defined hereinbefore,
which compounds of formula (I/j) may be:
either converted, by treating with formaldehyde in the presence of sodium cyanoborohydride, into compounds of formula (I/k), having a cis ring junction, a particular case of the compounds of formula (I):

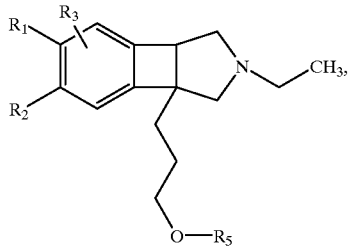

(I/k)

wherein $R_1$, $R_2$, $R_3$, and $R_5$ are as defined hereinbefore,
or treated, under conventional conditions of organic synthesis, with a compound of formula (IX):

R'$_4$-Z          (IX), wherein R'$_4$ has the same meanings as $R_4$ except hydrogen and benzyl, and Z represents a leaving group customarily used in organic synthesis,
to yield the compounds of formula (I/l), having a cis ring junction, a particular case of the compounds of formula (I):

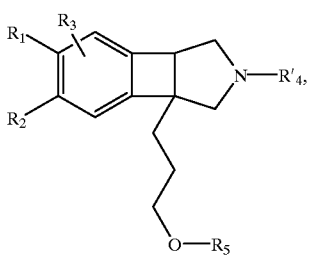

(I/l)

wherein $R_1$, $R_2$, $R_3$, $R'_4$ and $R_5$ are as defined hereinbefore, which compounds (I/a) to (I/l) constitute the totality of the compounds of the invention, which are purified, if necessary, according to a conventional purification technique, which may be separated, if desired, into their various isomers according to a conventional separation technique, and which are converted, where appropriate, into addition salts thereof with a pharmaceutically acceptable acid or base.

The compounds of formula (II) are products obtained from known substances according to known processes, as described hereinafter in Preparations 1 to 9. The Preparations are presented here by way of illustration without implying any limitation.

The compounds of formulae (V), (VIII) and (IX) are either commercial compounds or obtained according to conventional methods of organic synthesis.

The compounds of the present invention constitute inhibitors of serotonin reuptake and, because of that characteristic property, are useful in the treatment of depression, panic attacks, obsessive-compulsive disorders, phobias, impulsive disorders, drug abuse and anxiety.

Accordingly, the present invention relates also to pharmaceutical compositions comprising as active ingredient at least one compound of formula (I), its optical isomers or an addition salt thereof with a pharmaceutically acceptable acid or base, alone or in combination with one or more inert, non-toxic, pharmaceutically acceptable excipients or carriers.

Among the compositions according to the invention, there may be mentioned more especially those that are suitable for oral, parenteral (intravenous, intramuscular or subcutaneous), per- or trans-cutaneous, nasal, rectal, perlingual, ocular or respiratory administration, and especially tablets or dragees, sublingual tablets, sachets, gelatin capsules, lozenges, suppositories, creams, ointments, dermal gels, injectable or drinkable preparations, aerosols, eye drops, nose drops etc.

The dosage used varies according to the age and weight of the patient, the route of administration, the nature and severity of the disorder, and any associated treatments taken, and ranges from 0.5 mg to 50 mg in one or more administrations per day.

The Examples that follow illustrate the invention but do not limit it in any way.

The starting materials used are products that are known or prepared according to known procedures or are preparations that are described (Preparations 1 to 9).

The various synthesis Steps yield synthesis intermediates that are useful in preparing the compounds of the invention.

The structures of the compounds described in the Preparations, synthesis Steps and Examples were determined according to customary spectrophotometric techniques (infrared, NMR, mass spectrometry, . . . ).

The melting points were determined using either a Kofler hot-plate (K) or a hot-plate under a microscope (MK).

PREPARATION 1

4-(2-Bromophenyl)-3-cyano-N-benzylpyrrolidine

Step 1: 3-{Benzyl-[2-(2-bromophenyl)-2-oxoethyl]amino}propanenitrile

A solution of 97.5 g of 2-bromo-α-bromoacetophenone in 200 ml of acetone is poured dropwise, at ambient temperature, into a solution of 61.7 g de N-benzyl-2-cyanoethylamine and 67 ml of diisopropylethylamine in 200 ml of acetone. After stirring for 12 hours, the reaction mixture is evaporated, taken up in ether, washed twice with 500 ml of water each time and dried. After evaporating under reduced pressure, 131.9 g of expected product are obtained.

Step 2: 3-{Benzyl-[2-(2-bromophenyl)-2-hydroxyethyl]amino}propanenitrile

The 131.9 g of product obtained in Step 1 are dissolved in 300 ml of methanol and then added dropwise to 39.9 g of sodium borohydride in 300 ml of methanol. The temperature is maintained at 0° C. throughout the period of addition; the reaction mixture is then left at ambient temperature overnight and is subsequently evaporated to dryness, taken up in dichloromethane and washed with water. After concentrating under reduced pressure, chromatography on silica gel (dichloromethane) allows 94 g of expected product to be isolated.

Step 3: 3-{Benzyl-[2-(2-bromophenyl)-2-chloroethyl]amino}propanenitrile

The 94 g of product obtained in Step 2 are dissolved in 400 ml of methylene chloride. At ambient temperature, within a period of 1 hour, 90.5 ml of thionyl chloride are poured in dropwise. After stirring for 12 hours at ambient temperature, the reaction mixture is evaporated to dryness and then taken up in ether and filtered. The solid is taken up in 500 ml of 10% aqueous sodium carbonate solution and 1 litre of methylene chloride. After separating off, drying and evaporating under reduced pressure, 90.2 g of expected product are obtained.

Step 4: 4-(2-Bromophenyl)-3-cyano-N-benzylpyrrolidine

The 90.2 g of product obtained in Step 3 are dissolved in tetrahydrofuran. The solution is cooled to −70° C. and 143 ml of a 2M solution of sodium hexamethyldisilazide are poured in dropwise. After 1 hour at −70° C. and then 12 hours at ambient temperature, the reaction mixture is poured into 300 ml of saturated aqueous ammonium chloride solution and then extracted with ether. The combined organic phases are washed and dried. After evaporating, 78.5 g of expected product are obtained in the form of a mixture of diastereoisomers.

PREPARATION 2

4-(2-Bromo-4-methoxyphenyl)-3-cyano-N-benzypyrrolidine

A solution of N-butoxymethyl-N-trimethysilylmethylbenzylamine in 50 ml of dichloromethane is introduced, dropwise, into an E/Z mixture (70%/30%) of 2-bromo-4-methoxycinnamonitrile dissolved in 200 ml of dichloromethane, in the presence of a few drops of trifluoroacetic acid. The temperature increases to 40° C. That temperature is maintained for 1 hour 30 minutes. After returning to ambient temperature, 10 g of $K_2CO_3$ are added and then allowed to act for 30 minutes. After filtering and concentrating under reduced pressure, chromatography on silica gel (dichloromethane) allows 26 g of the expected product to be isolated in the form of a mixture of diastereoisomers in a proportion of 70%/30%.

PREPARATION 3

4-(2-Chloro-5-trifluoromethylphenyl)-3-cyano-N-benzylpyrrolidine

The product is obtained by following the procedure described in Preparation 2, using 2-chloro-5-trifluoromethyl-cinnamonitrile as substrate.

PREPARATION 4

4-(2-Bromo-5-fluorophenyl)-3-cyano-N-benzylpyrrolidine

The product is obtained by following the procedure described in Preparation 2, using 2-bromo-5-fluoro-cinnamonitrile as substrate.

PREPARATION 5

4-(2-Chloro-6-fluorophenyl)-3-cyano-N-benzylpyrrolidine

The product is obtained by following the procedure described in Preparation 2, using 2-chloro-6-fluoro-cinnamonitrile as substrate.

PREPARATION 6

4-(2-Chloro-4-fluorophenyl)-3-cyano-N-benzylpyrrolidine

The product is obtained by following the procedure described in Preparation 2, using 2-chloro-4-fluoro-cinnamonitrile as substrate.

PREPARATION 7

4-(2-Bromo-4,5-dimethoxyphenyl)-3-cyano-N-benzylpyrrolidine

The product is obtained by following the procedure described in Preparation 2, using 2-bromo-4,5-dimethoxy-cinnamonitrile as substrate.

PREPARATION 8

4-(2-Chloro-4,5-methylenedioxyphenyl)-3-cyano-N-benzylpyrrolidine

The product is obtained by following the procedure described in Preparation 2, using 2-chloro-4,5-methylenedioxy-cinnamonitrile as substrate.

PREPARATION 9

4-(2-Chloro-5-methoxyphenyl)-3-cyano-N-benzylpyrrolidine

The product is obtained by following the procedure described in Preparation 2, using 2-chloro-5-methoxy-cinnamornitrile as substrate.

EXAMPLE 1 cis-3a-[(3,4-Methylenedioxyphenoxy)methyl]-2,3,3a,7b-tetrahydro-1H-benzo[3,4]-cyclobuta[1,2-c]pyrrole and its hydrochloride Step A: cis-2-Benzyl-2,3,3a,7b-tetrahydro-1H-benzo[3,4]cyclobuta[1,2-c]pyrrole-3a-carboximidamide and its nitrate 78.4 g of the product of Preparation 1 dissolved in 50 ml of ether are introduced dropwise into sodium amide in 1.15 litres of liquid ammonia. After 3 hours of contact, 75 g of ammonium nitrate are added to the reaction mixture; the ammonia is then allowed to evaporate off. After taking up the residue in methylene chloride and water, the two phases are separated, the organic phase is dried over magnesium sulphate and the solvent is evaporated off. After trituration with ether and solidification with ethyl acetate, 42.2 g of expected product are obtained in the form of its nitrate.

Melting point: 183–187° C. (M.K).

Step B: cis-2-Benzyl-2,3,3a,7b-tetrahydro-1H-benzo[3,4] cyclobuta[1,2-c]pyrrole-3a-carboxamide 10.2 g of the product obtained in Step A are suspended, at ambient temperature, in 90 ml of ethanol. 30 ml of 1N sodium hydroxide solution and then 30 ml of water are added in succession. The mixture is refluxed for 2 hours and then evaporated to dryness. The residue is taken up in methylene chloride, washed with 200 ml of saturated aqueous sodium bicarbonate solution and dried over magnesium sulphate. After evaporation, 8.15 g of expected product are obtained.

Step C: cis-2-Benzyl-3a-methoxycarbonyl-2,3,3a,7b-tetrahydro-1H-benzo[3,4]-cyclobuta[1,2-c]pyrrole 8.10 g of the product obtained in Step B are dissolved in 90 ml of methanol. 11.6 ml of N,N-dimethylformamide dimethyl acetal are added and the mixture is left overnight, with stirring. A solution of hydrogen chloride in ethanol is then added, and evaporation to dryness is carried out. The residue is taken up in water and washed with ethyl acetate. The aqueous phase is rendered basic with sodium carbonate and then extracted with methylene chloride. After drying and evaporating, 8.1 g of expected product are obtained.

Step D: cis-2-Benzyl-3a-hydroxymethyl-2,3,3a,7b-tetrahydro-1H-benzo[3,4]cyclobuta[1,2-c]pyrrole A solution of 4 g of compound obtained in Step C in 50 ml of tetrahydrofuran is added dropwise to a suspension of 1.03 g of $LiAlH_4$ in 15 ml of tetrahydrofuran. The mixture is left overnight at ambient temperature. After hydrolysis and filtering off the salts, evaporation to dryness is carried out to obtain 3.5 g of expected product.

Step E: cis-2-Benzyl-3a-[(3,4-methylenedioxyphenoxy) methyl]-2,3,3a,7b-tetrahydro-1H-benzo[3,4]cyclobuta[1,2-c]pyrrole In a three-necked flask, 3.5 g of the compound obtained in Step D, 2 g of 3,4-methylenedioxyphenol and 3.8 g of triphenylphosphine are mixed in 40 ml of tetrahydrofuran. The mixture is cooled to 0° C. and 2.4 ml of diethyl azodicarboxylate are added dropwise over a period of 20 minutes. After reacting for 4 days at ambient temperature, the reaction mixture is concentrated under reduced pressure. Chromatography on silica gel ($CH_2Cl_2$/AcOEt: 95/5) allows 4.4 g of expected product to be isolated.

Step F: cis-3a-[(3,4-Methylenedioxyphenoxy)methyl]-2,3,3a,7b-tetrahydro-1H-benzo[3,4]cyclobuta[1,2-c]pyrrole and its hydrochloride 2.5 ml of 1-chloroethyl chloroformate are added to 4.4 g of the product obtained in Step E dissolved in 30 ml dichloroethane and the mixture is refluxed for 3 hours. The mixture is evaporated to dryness, taken up in 30 ml of methanol and refluxed overnight. After evaporation, chromatography on silica gel allows 1.45 g of expected product to be isolated, the hydrochloride of which is prepared.

Melting point (hydrochloride): 208–213° C. (M.K)

EXAMPLE 2 cis-2-Benzyl-5-methoxy-3a-[(3,4-methylenedioxyphenoxy)-methyl]-2,3,3a,7b-tetrahydro-1H-benzo[3,4]cyclobuta[1,2-c]pyrrole The procedure is as in Example 1, Steps A to E, using the product of Preparation 2 as substrate in Step A.

Melting point: 107–109° C. (M.K).

EXAMPLE 3 cis-5-Methoxy-3a-[(3,4-methylenedioxyphenoxy)-methyl]-2,3,3a,7b-tetrahydro-1H-benzo[3,4]cyclobuta[1,2-c]pyrrole and its hydrochloride The procedure is as in Step F of Example 1, starting from the product obtained in Example 2.

Melting point (hydrochloride): 218–223° C. (M.K.)

EXAMPLE 4 cis-5-Methoxy-2-methyl-3a-[(3,4-methylenedioxyphenoxy)-methyl]-2,3,3a,7b-tetrahydro-1H-benzo[3,4]cyclobuta[1,2-c]pyrrole 0.75 g of the product obtained in Example 3, in the form of the free base, is dissolved in 25 ml of methanol and 1.35 g of acetic acid. 0.6 ml of 37% formaldehyde in water and then 0.25 g of sodium cyanoborohydride are added. After reacting for 2 days at ambient temperature, the reaction mixture is concentrated, taken up in water, rendered basic with sodium hydroxide, extracted with ethyl acetate, washed with water and with brine, dried and concentrated. Recrystallisation from ethanol allows 0.42 g of expected product to be isolated.

Melting point: 94–96° C. (M.K.)

EXAMPLE 5 cis-6-Trifluoromethyl-3a-[(3,4-methylenedioxyphenoxy)methyl]-2,3,3a,7b-tetrahydro-1H-benzo[3,4]cyclobuta[1,2-c]pyrrole and its hydrochloride The procedure is as in Example 1, Steps A to F, using the product of Preparation 3 as substrate in Step A.

Melting point (hydrochloride): 186–190° C. (M.K.)

EXAMPLE 6 cis-6-Fluoro-3a-[(3,4-methylenedioxyphenoxy)-methyl]-2,3,3a,7b-tetrahydro-1H-benzo[3,4]cyclobuta[1,2-c]pyrrole and its hydrochloride The procedure is as in Example 1, Steps A to F, using the product of Preparation 4 as substrate in Step A.

Melting point (hydrochloride): 248–252° C. (M.K.)

EXAMPLE 7 cis-6-Fluoro-2-methyl-3a-[(3,4-methylenedioxyphenoxy)-methyl]-2,3,3a,7b-tetrahydro-1H-benzo[3,4]cyclobuta[1,2-c]pyrrole and its hydrochloride The procedure is as in Example 4, using the product of Example 6 as substrate.

Melting point: 212–216° C.; Elemental microanalysis

|  | C | H | N | Cl |
|---|---|---|---|---|
| % found | 62.66 | 5.40 | 3.90 | 10.16 |
| % calculated | 62.72 | 5.26 | 3.85 | 9.74 |

EXAMPLE 8 cis-7-Fluoro-3a-[(3,4-methylenedioxyphenoxy)-methyl]-2,3,3a,7b-tetrahydro-1H-benzo[3,4]cyclobuta[1,2-c]pyrrole and its hydrochloride The procedure is as in Example 1, Steps A to F, using the product of Preparation 5 as substrate in Step A.

Melting point (M.K.) 215–219° C.; Elemental microanalysis:

|  | C | H | N | Cl |
|---|---|---|---|---|
| % found | 61.94 | 5.16 | 3.94 | 10.29 |
| % calculated | 61.81 | 4.90 | 4.00 | 10.14 |

EXAMPLE 9 cis-5-Fluoro-3a-[(3,4-methylenedioxyphenoxy)-methyl]-2,3,3a,7b-tetrahydro-1H-benzo[3,4]cyclobuta[1,2-c]pyrrole and its hydrochloride The procedure is as in Example 1, Steps A to F, using the product of Preparation 6 as substrate in Step A.

Melting Point (M.K.): 196–198° C.; Elemental microanalysis:

|  | C | H | N | Cl |
|---|---|---|---|---|
| % found | 61.60 | 5.12 | 4.01 | 10.61 |
| % calculated | 61.81 | 4.90 | 4.00 | 10.14 |

EXAMPLE 10 cis-5,6-Dimethoxy-3a-[(3,4-methylenedioxyphenoxy)-methyl]-2,3,3a,7b-tetrahydro-1H-benzo[3,4]cyclobuta[1,2-c]pyrrole and its hydrochloride The procedure is as in Example 1, Steps A to F, using the product of Preparation 7 as substrate in Step A.

Melting point (M.K.): 202–206° C.; Elemental microanalysis:

|   | C | H | N | Cl |
|---|---|---|---|---|
| % found | 61.17 | 5.69 | 4.01 | 8.97 |
| % calculated | 61.30 | 5.66 | 3.57 | 9.05 |

EXAMPLE 11 cis-5,6-Methylenedioxy-3a-[(3,4-methylenedioxyphenoxy)-methyl]-2,3,3a,7b-tetrahydro-1H-benzo[3,4]cyclobuta[1,2-c]pyrrole and its hydrochloride The procedure is as in Example 1, Steps A to F, using the product of Preparation 8 as substrate in Step A.

Melting point (M.K.): 212–214° C.; Elemental microanalysis:

|   | C | H | N | Cl |
|---|---|---|---|---|
| % found | 60.53 | 4.98 | 4.10 | 9.04 |
| % calculated | 60.73 | 4.83 | 3.73 | 9.43 |

EXAMPLE 12

6-Methoxy-3a-[(3,4-methylenedioxyphenoxy)-methyl]-2,3,3a,7b-tetrahydro-1H-benzo[3,4]cyclobuta[1,2-c]pyrrole and its hydrochloride The procedure is as in Example 1, Steps A to F, using the product of Preparation 9 as substrate in Step A.

Melting point (M.K.): 162–164° C.; Elemental microanalysis:

|   | C | H | N | Cl |
|---|---|---|---|---|
| % found | 63.14 | 5.51 | 3.97 | 10.07 |
| % calculated | 63.07 | 5.57 | 3.87 | 9.80 |

EXAMPLE 13 cis-3a-[(2,1,3-Benzoxadiazol-5-yloxy)methyl]-2,3,3a,7b-tetrahydro-1H-benzo-[3,4]cyclobuta[1,2-c]pyrrole and its hydrochloride The procedure is as in Example 1, Steps A to F, using 2,1,3-benzoxadiazol-5-ol instead of 3,4-methylenedioxyphenol in Step E of that Example.

Melting point: 235–237° C.; Elemental microanalysis:

|   | C | H | N | Cl |
|---|---|---|---|---|
| % found | 61.55 | 5.00 | 12.46 | 10.82 |
| % calculated | 61.92 | 4.89 | 12.74 | 10.75 |

EXAMPLE 14 cis-3a-[(4-Cyclopentylphenoxy)methyl]-2,3,3a,7b-tetrahydro-1H-benzo[3,4]cyclobuta-[1,2-c]pyrrole The procedure is as in Example 1, Steps A to F, using 4-cyclopentylphenol instead of 3,4-methylenedioxyphenol in Step E of that Example.

Melting point: 80–82° C.; Elemental microanalysis:

|   | C | H | N |
|---|---|---|---|
| % found | 82.05 | 7.74 | 4.36 |
| % calculated | 82.72 | 7.89 | 4.38 |

EXAMPLE 15 cis-3a-{[(Thiochroman-4-on-6-yl)oxy]methyl}-2,3,3a,7b-tetrahydro-1H-benzo[3,4]-cyclobuta[1,2-c]pyrrole and its hydrochloride The procedure is as in Example 1, Steps A to F, using 6-hydroxy-thiochroman-4-one instead of 3,4-methylenedioxyphenol in Step E of that Example.

Melting point: 211–213° C.; Elemental microanalysis:

|   | C | H | N | Cl | S |
|---|---|---|---|---|---|
| % found | 64.44 | 5.50 | 3.96 | 9.24 | 8.32 |
| % calculated | 64.25 | 5.39 | 3.75 | 9.48 | 8.58 |

EXAMPLE 16 cis-3a-{[4-(1-Adamantyl)phenoxy]methyl}-2,3,3a,7b-tetrahydro-1H-benzo[3,4]cyclobuta[1,2-c]pyrrole and its hydrochloride The procedure is as in Example 1, Steps A to F, using 4-(1-adamantyl)phenol instead of 3,4-methylenedioxyphenol in Step E of that Example.

Melting point (M.K.): 244–248° C.; Elemental microanalysis:

|   | C | H | N | Cl |
|---|---|---|---|---|
| % found | 77.37 | 7.73 | 3.52 | 8.77 |
| % calculated | 76.85 | 7.64 | 3.32 | 8.40 |

EXAMPLE 17 cis-3a-[(5-Indanyloxy)methyl]-2,3,3a,7b-tetrahydro-1H-benzo[3,4]cyclobuta[1,2-c]-pyrrole and its hydrochloride The procedure is as in Example 1, Steps A to F, using 5-hydroxyindan instead of 3,4-methylenedioxyphenol in Step E of that Example.

Melting point (M.K.): 224–227° C.; Elemental microanalysis:

|   | C | H | N | Cl |
|---|---|---|---|---|
| % found | 73.17 | 6.92 | 4.43 | 11.19 |
| % calculated | 73.27 | 6.76 | 4.27 | 10.81 |

EXAMPLE 18 cis-3a-{[(4-Methyl-2H-chromen-2-one-7-yloxy]methyl}-2,3,3a,7b-tetrahydro-1H-benzo[3,4]cyclobuta[1,2-c]pyrrole and its hydrochloride The procedure is as in Example 1, Steps A to F, using 7-hydroxy-4-methyl-chromen-2-one instead of 3,4-methylenedioxyphenol in Step E of that Example.

Melting point (M.K.): 217–222° C.; Elemental microanalysis:

|  | C | H | N | Cl |
|---|---|---|---|---|
| % found | 68.38 | 5.85 | 3.84 | 9.77 |
| % calculated | 68.20 | 5.45 | 3.79 | 9.59 |

EXAMPLE 19 cis-3a-[(Chromen-2-one-7-yloxy)methyl]-2,3,3a,7b-tetrahydro-1H-benzo[3,4]cyclobuta[1,2-c]pyrrole and its hydrochloride The procedure is as in Example 1, Steps A to F, using 7-hydroxy-chromen-2-one instead of 3,4-methylenedioxyphenol in Step E of that Example.

Melting point (M.K.): 231–235° C.; Elemental microanalysis:

|  | C | H | N | Cl |
|---|---|---|---|---|
| % found | 67.38 | 5.61 | 3.98 | 10.49 |
| % calculated | 67.51 | 5.10 | 3.94 | 9.96 |

EXAMPLE 20 cis-3a-[(2-Ethoxyphenoxy)methyl]-2,3,3a,7b-tetrahydro-1H-benzo[3,4]cyclobuta-[1,2-c]pyrrole and its hydrochloride The procedure is as in Example 1, Steps A to F, using 2-ethoxyphenol instead of 3,4-methylenedioxyphenol in Step E of that Example.

Melting point (M.K.): 200–204° C.; Elemental mnicroanalysis:

|  | C | H | N | Cl |
|---|---|---|---|---|
| % found | 68.74 | 6.91 | 4.32 | 10.89 |
| % calculated | 68.77 | 6.68 | 4.22 | 10.68 |

EXAMPLE 21 cis-3a-[2-(3,4-Methylenedioxyphenoxy)ethyl]-2,3,3a,7b-tetrahydro-1H-benzo[3,4]-cyclobuta[1,2-c]pyrrole and its hydrochloride Step A: cis-2-Benzyl-3a-bromomethyl-2,3,3a,7b-tetrahydro-1H-benzo[3,4]cyclobuta-[1,2-c]pyrrole A mixture composed of 5.3 g of the product obtained in Step D of Example 1, 9 g of carbon tetrabromide and 7.2 g of triphenylphosphine in 115 ml of ether is refluxed for 24 hours. After cooling, filtering off the precipitate and concentrating, the residue obtained is purified by chromatography on silica gel (dichloromethane/ethanol:95/5), allowing the expected product to be isolated.

Step B: cis-2-Benzyl-3a-cyanomethyl-2,3,3a,7b-tetrahydro-1H-benzo[3,4]cyclobuta-[1,2-c]pyrrole 4.76 g of the product obtained in the previous Step A are dissolved in 75 ml of tetrahydrofuran, and then 6.26 g of tetrabutylammonium cyanide are added in portions. After 12 hours at ambient temperature, the mixture is diluted with 75 ml of ether and then poured onto 25 ml of saturated sodium bicarbonate solution. After separating off, washing with 1N hydrochloric acid and then rendering alkaline, the organic phases obtained by extracting with dichloromethane are washed, dried, filtered and then concentrated under reduced pressure, allowing the expected product to be isolated.

Step C: cis-(2-Benzyl-2,3,3a,7b-tetrahydro-1H-benzo[3,4]cyclobuta[1,2-c]pyrrol-3a-yl)acetic acid A mixture composed of 2.64 g of the compound obtained in Step B and 31 ml of 20% hydrochloric acid is heated at reflux for 4 hours; 31 ml of 20% hydrochloric acid are then added and refluxing is maintained for 6 hours 30 minutes. The mixture is evaporated, allowing the expected product to be isolated, which is used as such in the following Step.

Step D: cis-2-(2-Benzyl-2,3,3a,7b-tetrahydro-1H-benzo[3,4]cyclobuta[1,2-c]pyrrol-3a-yl)ethanol 3.32 g of the product obtained in Step C are introduced, in portions, into a suspension composed of 0.73 g of lithium aluminium hydride and 53 ml of tetrahydrofuran. After 2 hours at ambient temperature, the medium is hydrolysed in the cold state and the precipitate formed is filtered off. After evaporating off the solvent, the expected product is isolated.

Step E: cis-2-Benzyl-3a-[2-(3,4-methylenedioxyphenoxy)methyl]-2,3,3a,7b-tetrahydro-1H-benzo[3,4]cyclobuta[1,2-c]pyrrole The procedure is as in Step E of Example 1 using, as substrate, the product of Step D obtained above.

Step F: cis-3a-[2-(3,4-Methylenedioxyphenoxy)ethyl]-2,3,3a,7b-tetrahydro-1H-benzo[3,4]cyclobuta[1,2-c]pyrrole and its hydrochloride The procedure is as in Step F of Example 1 using, as substrate, the product of Step E obtained above.

Melting point: 204–207° C.; Elemental microanalysis:

|  | C | H | N | Cl |
|---|---|---|---|---|
| % found | 65.94 | 5.81 | 4.04 | 10.73 |
| % calculated | 65.99 | 5.83 | 4.05 | 10.23 |

EXAMPLE 22 cis-3a-[(1-cyanobenzocyclobutan-5-yloxy)methyl]-2,3,3a, 7b-tetrahydro-1H-benzo[3,4]cyclobuta[1,2-c] pyrrole and its hydrochloride The procedure is as in Example 1, Steps A to F, using 1-cyano-benzocyclobutan-5-ol instead of 3,4-methylenedioxyphenol in Step E of that Example.

Melting point (M.K.): 136–138° C.

EXAMPLE 23 cis-3a-[(3,5-bis-trifluoromethylphenoxy)methyl]-2,3, 3a,7b-tetrahydro-1H-benzo[3,4]cyclobuta[1,2-c] pyrrole and its hydrochloride The procedure is as in Example 1, Steps A to F, using 3,5-bis-trifluoromethylphenol instead of 3,4-methylenedioxyphenol in Step E of that Example.

Melting point (M.K.): 242–244° C.

EXAMPLE 24 cis-3a-[(3-dihydro-benzofuran-5yloxy)methyl]-2,3,3a,7b-tetrahydro-1H-benzo[3,4]cyclobuta[1,2-c]pyrrole and its hydrochloride The procedure is as in Example 1, Steps A to F, using 2,3-dihydro-benzofuran-5-ol instead of 3,4-methylenedioxyphenol in Step E of that Example.

Melting point (M.K.): 208° C. (décomposition)

EXAMPLE 25 cis-3a-[(2,3-dihydro-benzo[1,4]dioxan-6-yloxy)methyl]-2,3,3a,7b-tetrahydro-1H-benzo[3,4]cyclobuta[1,2-c]pyrrole and its hydrochloride The procedure is as in Example 1, Steps A to F, using 2,3-dihydro-benzo[1,4]dioxan-6-ol instead of 3,4-methylenedioxyphenol in Step E of that Example.

Melting point (M.K.): 219–222° C.

EXAMPLE 26 cis-3a-[(3,4-dimethylphenoxy)methyl]-2,3,3a,7b-tetrahydro-1H-benzo[3,4]cyclobuta[1,2-c]pyrrole and its hydrochloride The procedure is as in Example 1, Steps A to F, using 3,4-dimethylphenol instead of 3,4-methylenedioxyphenol in Step E of that Example.

Melting point (M.K.): 230–232° C.

EXAMPLE 27 cis-3a-[(3,4-dihydro-2H-thiochromen-7-yloxy)methyl]-2,3,3a,7b-tetrahydro-1H-benzo[3,4]cyclobuta[1,2-c]pyrrole and its hydrochloride The procedure is as in Example 1, Steps A to F, using 7-thiochromanol instead of 3,4-methylenedioxyphenol in Step E of that Example.

Melting point (M.K.): 248–250° C.

PHARMACOLOGICAL STUDY OF THE COMPOUNDS OF THE INVENTION

A. In vitro study

EXAMPLE 28

Determination of the Affinity for Serotonin Reuptake Sites

The affinity was determined by competition experiments using [$^3$H]-paroxetine (NEN, Les Ulis, France). The membranes are prepared from rat frontal cortex and are incubated in triplicate with 1.0 nM [$^3$H]-paroxetine and cold ligand in a final volume of 0.4 ml, for 2 hours at 25° C. The incubation buffer contains 50 nM TRIS-HCl (pH 7.4), 120 mM NaCl and 5 mM KCl. The non-specific binding is determined using 10 $\mu$M citalopram. At the end of the incubation, the incubation medium is filtered and washed three times with 5 ml of cooled buffer. The radioactivity retained on the filters is determined by liquid scintillation counting. The binding isotherms are analysed by non-linear regression to determine the IC$_{50}$ values. Those values are converted into a dissociation constant ($K_i$) using the Cheng-Prusoff equation:

$$K_i = IC_{50}/(1+L/K_d)$$

wherein L is the concentration of [$^3$H]-paroxetine and $K_d$ is the dissociation constant of [$^3$H]-paroxetine for the serotonin reuptake site (0.13 nM). The results are expressed in p$K_i$ (–log $K_i$).

The compounds of the present invention demonstrate very good affinity for the serotonin reuptake sites. By way of example, the p$K_i$ of the compound of Example 1 is 7.9.

B. In vivo study

EXAMPLE 29

Microdialysis Experiment in the Rat

Rats are anaesthetised with pentobarbital (60 mg/kg i.p.). They are placed in a Kopf stereotaxic device and the cannula guide is implanted in the cingulate frontal cortex in accordance with the coordinates described in the Paxinos and Watson atlas (1982) as follows: AP=+2.2; L=±0.6; DV=–0.2. The rats are placed in separate cages and are not used in dialysis until 5 days later. On the day of the dialysis, the probe is slowly lowered and held in position. The probe is perfused at a flow rate of 1 $\mu$l/min. with a solution of 147.2 mM NaCl, 4 mM KCl and 2.3 mM CaCl$_2$ adjusted to pH 7.3 with a phosphate buffer (0.1 M). Two hours after implantation, samples are collected every 20 minutes for 4 hours. Three baseline samples are taken before administration of the products to be tested. The rats are left in their individual cages for the whole of the experiment. When the experiment is finished, the rats are decapitated and the brain is removed and frozen in isopentane. Sections of a thickness of 100 $\mu$m are cut and stained with cresyl violet, which allows verification of the location of the probes. The simultaneous quantification of dopamine, norepinephrine and serotonin is carried out as follows: 20 $\mu$l of dialysis sample are diluted with 20 $\mu$l of mobile phase (NaH$_2$PO$_4$: 75 mM; EDTA: 20 $\mu$M; sodium 1-decanesulphonate: 1 mM; methanol: 17.5%; triethylamine: 0.01%; pH: 5.70) and 33 $\mu$l are analysed by HPLC with a reverse phase column thermostatically maintained at 45° C. and are quantified by means of a coulometric detector. The potential of the first electrode of the detector is set at –90 mV (reduction) and the second at +280 mV (oxidation). The mobile phase is injected with a pump at a flow rate of 2 ml/min. The sensitivity limits for dopamine, norepinephrine and serotonin are 0.55 fmole per sample. All the products of the invention are injected subcutaneously in a volume of 1.0 ml/kg. The products are dissolved in distilled water to which a few drops of lactic acid have been added if necessary.

Results:

By way of example, and in order to illustrate the activity of the products of the invention, the compound of Example 1, administered subcutaneously at a dose of 10 mg/kg, increases the levels of serotonin, dopamine and noradrenaline by:

+226.3%±20.1; +54.8%±6.4 and +96.4%±7.8, respectively (maximum % of the effect compared with the baseline level defined as 0%).

EXAMPLE 30

Test of Aggressiveness in Isolated Mice

This test allows the evaluation of the intraspecies anti-aggressive activity of a product in mice that have been kept in isolation for several months.

Animals:

The test uses male CD mice (Charles River) weighing from 22 to 25 g when they arrive at the animal house. On their arrival, the animals are isolated in individual cages made of opaque black polycarbonate (23×14×13 cm) with a grill lid, and are housed for a prolonged period (approximately six months) in the experimentation room.

Selection of pairs of mice:

The selection of aggressive pairs of mice that will be used for an extended period in the study commences after the animals have been isolated for one month. Once or twice per week a mouse from another cage (intruder) is placed in the cage of a (resident) mouse and the two animals are observed to see if they attack one another (sniffing, pursuing, nicking, biting) during that trial. At the end of the trial (maximum duration 10 minutes), each mouse is isolated again in its own cage. If attacks have occurred, the same pair will be tested again in the next trial; if there have been no attacks, each mouse of that pair will be placed in the presence of another mouse in the subsequent trial. Thus, in the course of successive trials carried out at a rate of 1 or 2 per week, definitive pairs of mice that will be used for the experiments are selected. The selection of the pairs is based on the stability of the combative nature of the animals from one trial to the next, the shortness of the latent period of the first attack and the frequency and duration of the attacks. With the pairs selected in that manner, those parameters are checked each week by a rapid trial, without treatment, two days before the Test day.

Test:

The test takes place once a week. 30 minutes before being placed together, the two mice of the pair each receive the same treatment (product or solvent) and remain isolated in their respective cages. At T0 min., the intruder mouse is introduced into the cage of the resident mouse for a period of 3 minutes. The latent period (in seconds) of the first attack and the number and total duration (in seconds) of the attacks are recorded. Any reversal in the dominance of one mouse in relation to the other is also noted (in general, the resident mouse is the dominant mouse). At the end of the test, the intruder mouse returns to its cage; the animals remain in isolation until the next rapid trial and test the following week. The Inhibitory Dose 50 of the number or duration of the attacks is that dose of product which reduces by half the average of each of those values compared with those obtained respectively in the control group.

Results:

By way of example and in order to illustrate the activity of the products of the invention, the Inhibitory Dose 50 for the compound of Example 1 is less than 5 mg/kg i.p.

What is claimed is:

1. A compound, with a cis ring junction, selected from those of the formula (I):

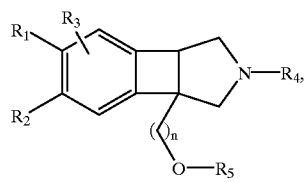

(I)

wherein:

R$_1$, R$_2$ and R$_3$, which may be the same or different, each independently of the others represents a substituent selected from hydrogen, halogen, linear or branched (C$_1$–C$_6$)alkyl, linear or branched (C$_2$–C$_6$)alkenyl, linear or branched (C$_2$–C$_6$)alkynyl, hydroxy, linear or branched (C$_1$–C$_6$)alkoxy, cycloalkyl, cycloalkyl-(C$_1$–C$_6$)alkyl in which alkyl is linear or branched, aryl, aryl-(C$_1$–C$_6$)alkyl in which alkyl is linear or branched, aryloxy, aryl-(C$_1$–C$_6$)alkoxy in which alkoxy is linear or branched, linear or branched (C$_1$–C$_6$)trihaloalkyl, linear or branched (C$_1$–C$_6$)trihaloalkoxy, cyano, nitro, —OSO$_2$CH$_3$, —OSO$_2$CF$_3$, —NR$_6$R$_7$, and —CO$_2$R$_6$ wherein R$_6$ and R$_7$, which may be the same or different, each independently of the other represents a substituent selected from hydrogen, linear or branched (C$_1$–C$_6$) alkyl, linear or branched (C$_2$–C$_6$)alkenyl, linear or branched (C$_2$–C$_6$)alkynyl, cycloalkyl, cycloalkyl-(C$_1$–C$_6$)alkyl in which alkyl is linear or branched, aryl, and aryl-(C$_1$–C$_6$)alkyl in which alkyl is linear or branched, or two of R$_1$, R$_2$ and R$_3$ in adjacent positions represent, together with common atoms of the benzene ring to which they are bonded, a saturated or unsaturated (C$_4$–C$_8$)-ring wherein one or two carbon is/are optionally replaced by one or two hetero atoms, which may be the same or different, selected from oxygen, nitrogen, and sulphur, it being understood that in the case where two of R$_1$, R$_2$ and R$_3$ in adjacent positions have the meaning mentioned hereinbefore, the remaining substituent R$_1$ or R$_2$ or R$_3$ takes one of the above-mentioned individual definitions of those substituents, R$_4$ represents a group selected from hydrogen, linear or branched (C$_1$–C$_6$)alkyl, linear or branched (C$_2$–C$_6$) alkenyl, linear or branched (C$_2$–C$_6$)alkynyl, cycloalkyl, cycloalkyl-(C$_1$–C$_6$)alkyl in which alkyl is linear or branched, aryl, aryl-(C$_1$–C$_6$)alkyl in which alkyl is linear or branched, heterocycloalkyl, heterocycloalkyl-(C$_1$–C$_6$)alkyl in which alkyl is linear or branched, heteroaryl, and heteroaryl-(C$_1$–C$_6$)alkyl in which alkyl is linear or branched, R$_5$ represents a group selected from aryl, optionally substituted aryl, heteroaryl, and optionally substituted heteroaryl, n represents an integer of 1 to 3 inclusive, its isomers and addition salts thereof with a pharmaceutically-acceptable acid or base, cycloalkyl being understood to mean a (C$_3$–C$_8$)-ring, which may be mono- or bi-cyclic, optionally having one or more unsaturated bond(s), the said unsaturated bond(s) not conferring an aromatic character on the ring, which is optionally substituted by one or more substituents, which may be the same or different, selected from halogen, and linear or branched (C$_1$–C$_6$) alkyl, heterocycloalkyl being understood to mean optionally substituted cycloalkyl as defined hereinbefore and containing, in the ring, one, two or three hetero atoms, which may be the same or different, selected from oxygen, nitrogen, and sulphur, furthermore, aryl being understood to mean phenyl, naphthyl, dihydronaphthyl, tetrahydronaphthyl, indenyl, or indanyl, and optionally substituted aryl being understood to mean aryl, as defined hereinbefore, optionally substituted by one or more substituents, which may be the same or different, selected from halogen, hydroxy, linear or branched (C$_1$–C$_6$)alkyl, linear or branched (C$_1$–C$_6$)alkoxy, linear or branched (C$_1$–C$_6$)alkenyl, cycloalkyl, adamantyl, cycloalkyl-(C$_1$–C$_6$)alkyl in which alkyl is linear or branched, aryl, aryl-(C$_1$–C$_6$)alkyl in which alkyl is linear or branched, aryloxy, aryl-(C$_1$–C$_6$)alkoxy in which alkoxy is linear or branched, linear or branched (C$_1$–C$_6$)trihaloalkyl, linear or branched (C$_1$–C$_6$)trihaloalkoxy, cyano, nitro, oxo, —OSO$_2$CH$_3$, —OSO$_2$CF$_3$, —NR$_6$R$_7$, and —CO$_2$R$_6$ wherein R$_6$ and R$_7$ are as defined hereinbefore for formula (I), heteroaryl being likewise understood to mean aryl as defined hereinbefore containing one, two, or three heteroatoms, which may be the same or different, selected from oxygen, nitrogen, and sulphur, and optionally substituted heteroaryl being understood to mean heteroaryl as defined hereinbefore optionally substituted by one or more substituents; which may be the same or different, as defined for substitutes of aryl.

2. A compound of claim 1, wherein R$_5$ represents heteroaryl.

3. A compound of claim 1, wherein R$_5$ represents methylenedioxyphenyl or ethylenedioxyphenyl.

4. A compound of claim 1, wherein n is 1.

5. A compound of claim 1, wherein n is 2.

6. A compound of claim 1, wherein R$_4$ represents hydrogen, linear or branched (C$_1$–C$_6$)alkyl, or aryl-(C$_1$–C$_6$) alkyl in which alkyl is linear or branched.

7. A compound of claim 1, which is selected from cis-3a-[(3,4-methylenedioxyphenoxy)methyl]-2,3,3a,7b-tetrahydro-1H-benzo[3,4]cyclobuta[1,2-c]pyrrole, and its hydrochloride salt.

8. A compound of claim 1, which is cis-2-benzyl-5-methoxy-3a-[(3,4-methylenedioxyphenoxy)-methyl]-2,3,3a,7b-tetrahydro-1H-benzo[3,4]cyclobuta[1,2-c]pyrrole.

9. A compound of claim 1, which is selected from cis-5-methoxy-3a-[(3,4-methylenedioxyphenoxy)-methyl]-2,3,3a,7b-tetrahydro-1H-benzo[3,4]cyclobuta[1,2-c]pyrrole, and its hydrochloride salt.

10. A compound of claim 1, which is cis-5-methoxy-2-methyl-3a-[(3,4-methylenedioxyphenoxy)-methyl]-2,3,3a,7b-tetrahydro-1 H-benzo[3,4]cyclobuta[1,2-c]pyrrole.

11. A compound of claim 1, which is selected from cis-6-trifluoromethyl-3a-[(3,4-methylenedioxyphenoxy)-methyl]-2,3,3a,7b-tetrahydro-1H-benzo[3,4]cyclobuta[1,2-c]-pyrrole, and its hydrochloride salt.

12. A compound of claim 1 which is selected from cis-6-fluoro-3a-[(3,4-methylenedioxyphenoxy)-methyl]-2,3,3a,7b-tetrahydro-1H-benzo[3,4]cyclobuta[1,2-c]pyrrole, and its hydrochloride salt.

13. A pharmaceutical composition useful for treatment of depression comprising as active principle an effective amount of a compound as claimed in claim 1, in combination with one more pharmaceutically-acceptable excipients or carriers.

14. A method for treating a living body afflicted with a condition selected from depression, panic attacks, obsessive-compulsive disorders, phobias, impulsive disorders, drug abuse or anxiety, comprising the step of administering to the living body an amount of a compound of claim 1 which is effective as an inhibitor of serotonin recapture an for alleviation of said condition.

* * * * *

UNITED STATES PATENT AND TRADEMARK OFFICE
CERTIFICATE OF CORRECTION

PATENT NO. : 6,153,640
DATED : November 28, 2000
INVENTOR(S) : J-L. Peglion, B. Goument, A. Dessinges, M. Millan, J-M. Rivet, A. Dekeyne:

It is certified that error appears in the above-identified patent and that said Letters Patent is hereby corrected as shown below:

Title page,
Item [57], Abstract,
Line 13, "are usefull" should read -- which are useful --.
Line 14, "disease like" should be deleted.

Column 6,
Line 55, (formula (I/f): "N H" at far right of formula should read -- N    H --.

Column 7,
Line 6, (formula (I/g): "N CH₃," should read -- N    CH₃ --.

Column 8,
Line 25, (formula (I/j): "N H" should read -- N    H --.
Line 45, (formula (I/k): "N CH₃" should read -- N    CH₃ --.

Column 11,
Line 60, "cinnamornitrile" at the beginning of the line, should read
-- cinnamonitrile -- ,.
Line 64, "-cyclobutal[1,2-c]" should read -- -cyclobuta[1,2-c] --.

Column 17,
Line 39, "mni-" at the end of the line, should read -- mi- --.

Column 19,
Line 3, "cis-3a-[(3-" at the beginning of the line, should read -- cis-3a-[(2,3 --.

Column 22,
Line 25, "a group" should read -- a substituent --.

UNITED STATES PATENT AND TRADEMARK OFFICE
CERTIFICATE OF CORRECTION

PATENT NO. : 6,153,640
DATED : November 28, 2000
INVENTOR(S) : J-L. Peglion, B. Goument, A. Dessinges, M. Millan, J-M. Rivet, A. Dekeyne:

It is certified that error appears in the above-identified patent and that said Letters Patent is hereby corrected as shown below:

Column 24,
Line 27, "recapture an for" should read -- recapture and for --.

Signed and Sealed this

Thirteenth Day of November, 2001

Attest:

NICHOLAS P. GODICI
Acting Director of the United States Patent and Trademark Office Attesting Officer

UNITED STATES PATENT AND TRADEMARK OFFICE
CERTIFICATE OF CORRECTION

PATENT NO.     : 6,153,640
DATED          : November 28, 2000
INVENTOR(S)    : Jean-Louis Peglion et al.

It is certified that error appears in the above-identified patent and that said Letters Patent is hereby corrected as shown below:

Title page,
Item [57], ABSTRACT,
Line 13, "are useful" should read -- which are useful --.
Line 14, "diseases like" should be deleted.

Column 6,
Line 55, (formula(I/f): "  " should read -- N—H --.

Column 7,
Line 6, (formula (I/g): "  " should read -- N—CH$_3$ --.

Column 8,
Line 25, (formula(I/j): "  " should read -- N—H --.
Line 45, (formula (I/k): "  " should read -- N—CH$_3$ --.

Column 11,
Line 60, "cinnamornitrile" should read -- cinnamonitrile --.
Line 64, "cyclobutal[1,2-c]" should read -- cyclobuta[1,2-c] --.

Column 17,
Line 39, "mni" should read -- mi --.

Column 19,
Line 3, "cis-3a-[(3" should read -- cis-3a-[(2,3 --

Column 22,
Line 25, "a group" should read -- a substituent --.

UNITED STATES PATENT AND TRADEMARK OFFICE
CERTIFICATE OF CORRECTION

PATENT NO.    : 6,153,640
DATED         : November 28, 2000
INVENTOR(S)   : Jean-Louis Peglion et al.

It is certified that error appears in the above-identified patent and that said Letters Patent is hereby corrected as shown below:

<u>Column 24,</u>
Line 27, "recapture an for" should read -- recapture and for --.

This certificate supersedes Certificate of Correction issued November 13, 2001.

Signed and Sealed this

Eleventh Day of June, 2002

*Attest:*

*Attesting Officer*

JAMES E. ROGAN
*Director of the United States Patent and Trademark Office*